United States Patent [19]

Sahi et al.

[11] Patent Number: 4,828,547
[45] Date of Patent: May 9, 1989

[54] SELF-BLUNTING NEEDLE ASSEMBLY AND DEVICE INCLUDING THE SAME

[75] Inventors: Carl R. Sahi, Coventry; Richard R. Phillips, West Hartford; Chester Fudge, Rockfall; Jeffrey J. Lamo, Newington, all of Conn.

[73] Assignee: Bio-Plexus, Inc., Coventry, Conn.

[21] Appl. No.: 101,610

[22] Filed: Sep. 28, 1987

[51] Int. Cl.$^4$ .............................................. A61M 5/00
[52] U.S. Cl. ..................................... 604/110; 604/164
[58] Field of Search ............... 604/110, 158, 164, 165, 604/170, 181, 187, 192, 209, 210, 267, 272–274

[56] References Cited

U.S. PATENT DOCUMENTS

| | | | |
|---|---|---|---|
| 2,623,520 | 12/1952 | Bamford, Jr. et al. | 604/165 |
| 2,623,521 | 12/1952 | Shaw | 604/170 |
| 3,344,786 | 10/1967 | Berg et al. | 604/181 |
| 3,491,756 | 1/1970 | Bentov | 604/164 |
| 3,809,081 | 5/1974 | Loveless | 604/170 |
| 4,233,975 | 11/1980 | Yerman | 604/110 |
| 4,274,408 | 6/1981 | Nimrod | 604/165 |
| 4,509,945 | 4/1985 | Krammann et al. | 604/170 |
| 4,529,399 | 7/1985 | Groshong et al. | 604/170 |
| 4,731,068 | 3/1988 | Hesse | 604/110 |

Primary Examiner—Stephen C. Pellegrino
Assistant Examiner—Ralph Lewis
Attorney, Agent, or Firm—Victor E. Libert

[57] ABSTRACT

A self-blunting needle assembly comprises a hollow needle, which may be of conventional construction having a needle mouth and a needle shank terminating in a puncture tip, has mounted within it a blunting member including an elongate probe which slidably fits within the bore of the needle shank. The probe terminates in a distal tip which is initially positioned short of the puncture tip of the needle so as not to interfer with injection of the needle either into a patient or into a connecting device. After injection, the blunting member is advanced to an extended position in which its distal tip protrudes beyond the puncture tip, thereby effectively blunting the needle. This protruding probe disables the needle from a re-use and blunts it sufficiently to prevent or greatly reduce accidental needlestick wounds. A mechanical extension member, such as a pin or fluid flowing through the needle may be used to advance the blunting member to its extended position.

29 Claims, 5 Drawing Sheets

U.S. Patent    May 9, 1989    Sheet 1 of 5    4,828,547
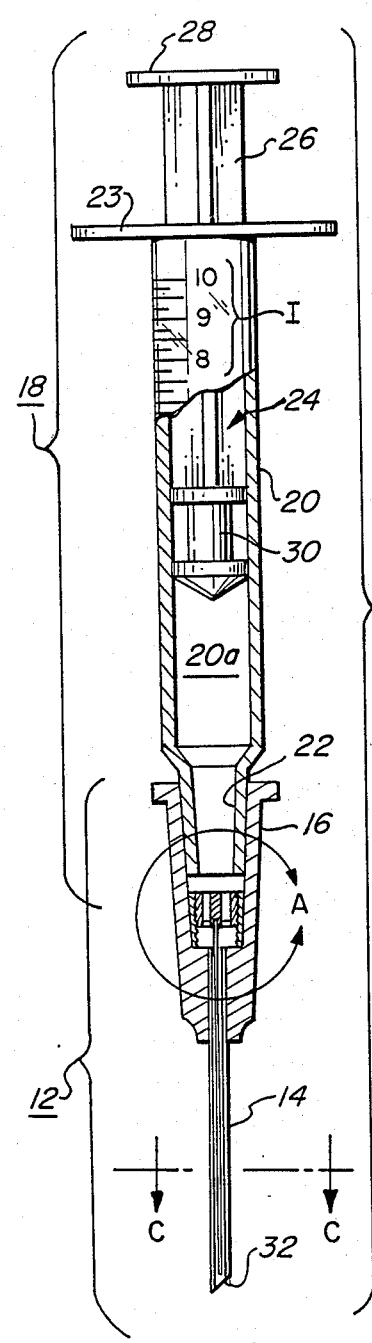
FIG. 1
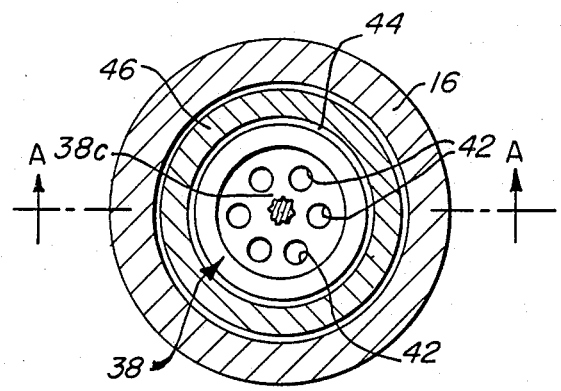
FIG. 1B
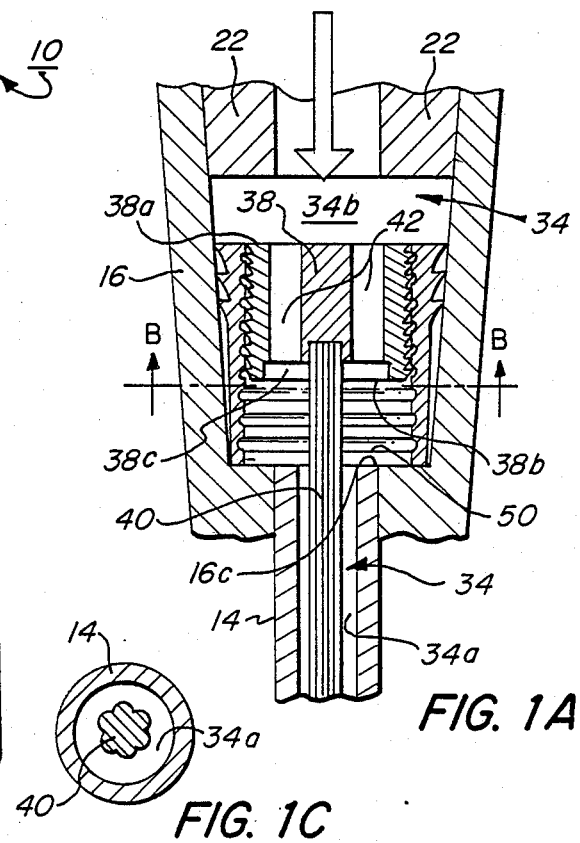
FIG. 1A
FIG. 1C

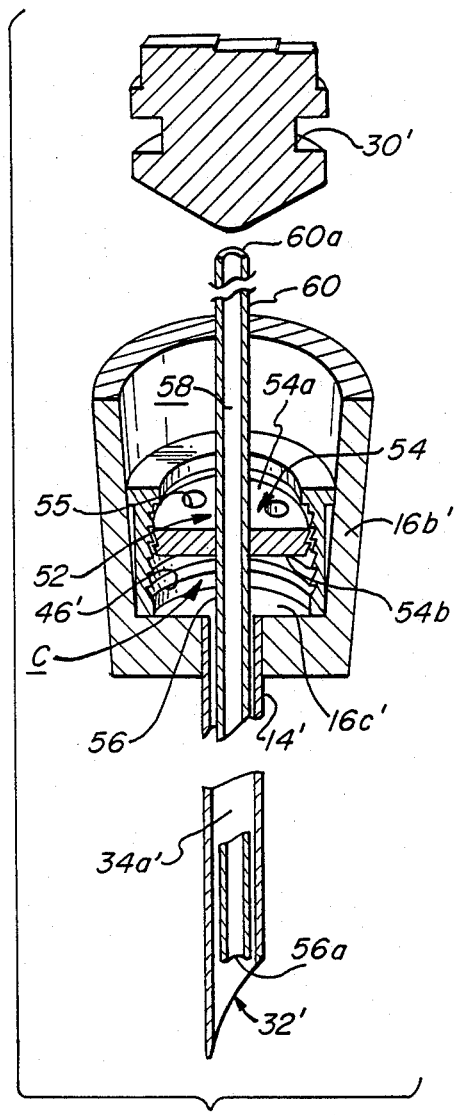
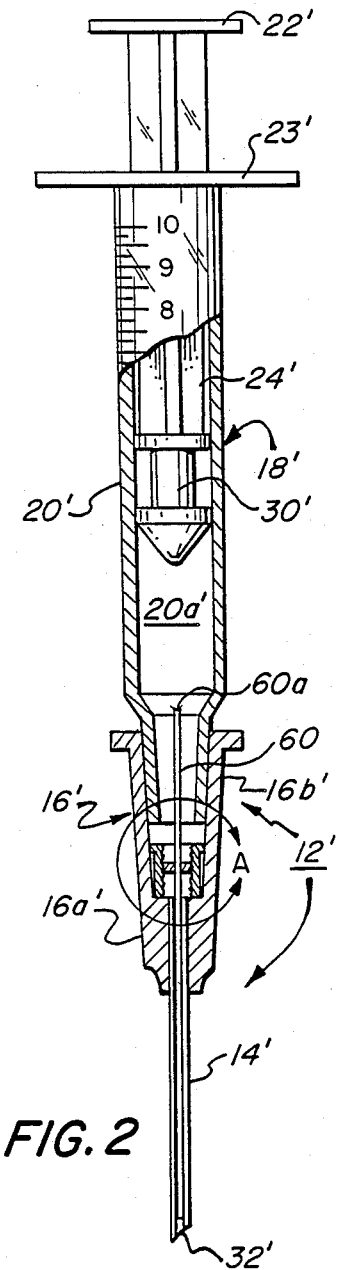
FIG. 2A
FIG. 2

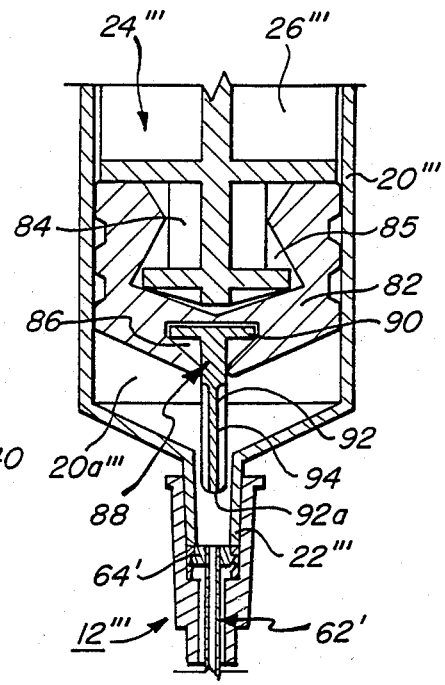
FIG. 4
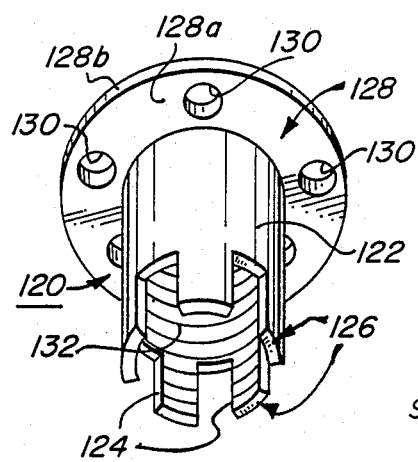
FIG. 6
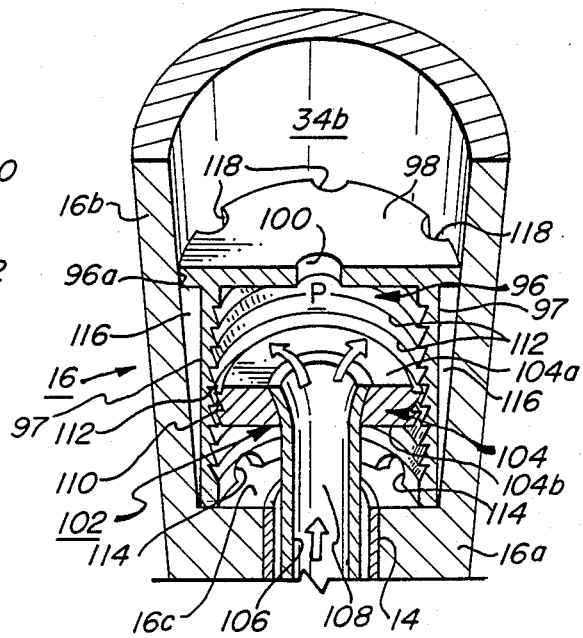
FIG. 6A
FIG. 5

SELF-BLUNTING NEEDLE ASSEMBLY AND DEVICE INCLUDING THE SAME

BACKGROUND OF THE INVENTION

1. Field Of The Invention

The present invention is concerned with a self-blunting needle assembly especially suited for use as a hypodermic needle, and with hypodermic syringes including such needle assemblies. More particularly, the present invention is concerned with a needle assembly which is self-blunting and disabled after a single use.

2. Description of Related Art

Hypodermic syringes designed to prevent reuse, i.e., designed to be effective for only a single use, are known. For example, U.S. Pat. 4,367,738 discloses a hypodermic syringe in which the plunger rod is fitted with flexible spikes which expand as the plunger is depressed in order to lock the plunger rod within the barrel portion of the syringe, thereby preventing retraction of the plunger rod for reuse of the syringe U.S. Pat. No. 3,478,937 discloses a syringe in which the plunger stem 23 has a collar unit 25 secured thereon which, when the plunger is pushed through the barrel 11 of the hypodermic syringe, passes through ring 22 mounted at one end of the barrel to prevent subsequent retraction of the plunger for re-use of the device.

U.S. Pat. No. 4,233,975 discloses a syringe in which a plug is positioned in or adjacent to the mouth of the needle so that movement of the plunger rod to expel fluid from the syringe seats a plug which blocks the liquid flow path from the syringe barrel to the needle mouth, thereby disabling the device from further use.

U.S. Pat. No. 4,391,273 discloses a hypodermic syringe in which the plunger carries a protruding pin 67 which punctures a lower wall of the barrel in order to prevent reuse of the hypodermic syringe.

U.S. Pat. No. 1,654,905 discloses a measuring syringe in which a tapering needle 9 has an enlarged head 10 and is mounted for sliding movement within a hollow tube 3, between the positions shown in FIGS. 2 and 3 of the patent. As explained beginning at page 1, line 72 of the patent, the needle 9 acts as a valve to meter a premeasured quantity of liquid into tube 3, and seats with the tip 16 of the needle 9 extending beyond the tip of tube 3 The syringe is then placed against the surface onto which fluid is to be applied and this forces back the tip 16, expelling liquid from the tube 3.

The art also shows syringes which are equipped with means intended to prevent accidental sticking of persons, such as the operator, with the needle. It is estimated that over 2,000 accidental needle-stick wounds are sustained by health care workers in the United States each day. The problem is aggravated by the trend of moving treatment out of hospitals and into doctors' offices and neighborhood clinics as part of a program to reduce health care costs. This trend increases the number and dispersion of health care workers who administer injections and draw blood samples, while reducing the frequency of such injections per individual health care worker. As a consequence, a larger number of less experienced people are administering injections and/or taking blood samples Although in the past an occasional serious illness such as that caused by the hepatitis B virus was sustained as a result of an accidental needle-stick wound, the problem was not considered to be a serious one until the advent of the spreading of human immunodeficiency virus (HIV) infection and the knowledge that this virus is transmissible to health care workers through needle-stick wounds from a contaminated needle. The HIV causes acquired immune deficiency syndrome (AIDS), a disease which, insofar as is presently known, is invariably fatal and which has already killed tens of thousands and infected possibly millions more. HIV is often referred to simply as "the AIDS virus" and the Surgeon General of the United States of America noted in a published (September, 1987) interview that there is no better way to become infected with the AIDS virus than to take blood from an AIDS patient and accidentally inflict a needle-stick wound with the contaminated needle.

This situation has stimulated activity to develop devices which reduce or eliminate the possibility of accidental needle-stick wounds without excessively increasing the unit cost of needles. U.S. Pat. No. 3,890,971 discloses a single use, safety syringe which includes a plunger which is permanently lockable by detent members when the plunger has been operated to expel liquid from the barrel portion of the syringe. The disclosed structure further includes a slidable needle cap which is also permanently lockable by detent members to encase the needle within the sleeve.

Brochures distributed by ICU Medical Inc., of Mission Viejo, Calif., show a hypodermic syringe which has a sheath carried on the needle. Insofar as can be discerned from the brochure, which contains the notation "Patent Pending", the needle extends beyond the sheath for use, and the sheath is grasped by the operator upon withdrawing the needle in order to retract the needle within the sheath upon withdrawal of the needle from the patient In this way, the sheath guards against accidental pricking of the operator with the withdrawn needle.

SUMMARY OF THE INVENTION

Generally, the present invention provides for a needle assembly containing a blunting member which is movable, either by fluid flow through the needle or by mechanical pressure, e.g., mechanical pressure applied by the plunger of the hypodermic syringe, from a retracted position in which the blunting member probe does not interfere with the puncture tip of the needle, to an extended position, attained after injection of the needle, in which the probe extends beyond the puncture tip thereby self-blunting the needle Preferably, the blunting member is moved to its extended position prior to removing the needle so that the possibility of an accidental stick-wound is avoided. The devices of the present invention will usually be employed to inject liquids such as medications into patients or to withdraw body fluids therefrom. In some cases, they may be used to inject or withdraw gases although withdrawn gases will usually contain liquids entrained therein.

In accordance with the present invention there is provided a self-blunting needle assembly device which is suitable for attachment to a fluid flow means, such as a hypodermic syringe, pump, vacuum pump or the like for flowing fluids such as body fluids or liquids. The device comprises the following components A needle member terminates in a puncture tip and has a needle bore extending therethrough and defining a fluid flow path extending through the needle to the puncture tip. A blunting member is comprised of an elongate probe having a transfer means associated therewith, the blunting member being mounted within the needle member for movement of the probe by the transfer means axially along the needle bore from a retracted position in which the probe is short of the puncture tip to an extended position in which the probe protrudes outwardly of and thereby blunts the puncture tip. The probe is dimensioned and configured to be accommodated within the needle bore while leaving the bore open to fluid flow therethrough. Locking means forming part of the assembly are dimensioned and configured to engage the blunting member and retain it in its extended position.

In one aspect of the invention, the transfer means comprises a piston from which the probe axially extends, and the blunting member is mounted with its piston disposed in the fluid flow path for movement of the blunting member to its extended position by fluid flowing through the flow path. The transfer means may be dimensioned and configured to drive the blunting member from its retracted position to its extended position by outflow movement of fluid, e.g., liquid, along the flow path, i.e., in the direction from the mouth to the puncture tip, or it may be dimensioned and configured to so drive the blunting member by inflow movement of fluid, e.g., liquid, along the flow path, i.e., in the direction from the puncture tip to the mouth. The piston may have one or more flow passages extending therethrough to permit the passage of liquid along the flow path past the piston.

In another aspect of the invention, the transfer means comprises an extension member mounted within the needle member to transfer mechanical force applied to the extension member to the blunting member, for movement thereof to its extended position.

In another aspect of the invention, the probe and the needle bore are each dimensioned and configured to provide therebetween an annular clearance for passage of liquid around the probe and through the needle bore. In a related aspect of the invention, the blunting member has a probe bore extending therethrough to define at least a segment of the fluid flow path through the needle member.

In accordance with another aspect of the invention, there is provided an improvement in a hypodermic syringe device comprising (i) a hollow needle member having a shank which terminates in a puncture tip and through which a needle bore extends, (ii) a barrel member providing a liquid reservoir and connected in liquid flow communication with the needle, and (iii) pressurizing means to impel liquid along a liquid flow path including the barrel member and the needle bore. The improvement comprises providing the syringe device with a needle assembly, blunting member and locking means substantially as described above.

Other aspects of the invention are set forth in the drawings and in the detailed description given below.

As used herein and in the claims, the following terms have the stated meanings.

The term "outflow" used to characterize the direction of fluid or liquid flow through a needle member, syringe or the like means such flow therethrough in a fluid-dispensing direction, i.e., in the direction from the needle mouth towards the puncture tip of the needle.

The term "inflow" used as above, means such fluid flow in a sample-taking direction, i.e., fluid flow in the direction from the puncture tip of the needle towards the needle mouth.

BRIEF DESCRIPTION OF THE DRAWINGS

FIG. 1 is an elevation view partially in cross section of a hypodermic syringe having one embodiment of a needle member of the invention attached thereto;

FIG. 1A is a view in cross section on an enlarged scale of portion A of the needle of FIG. 1;

FIG. 1B is a view taken along line B—B of FIG. 1A;

FIG. 1C is a cross-sectional view taken along line C—C of FIG. 1;

FIG. 2 is a view corresponding to FIG. 1 but showing another embodiment of the present invention;

FIG. 2A is an enlarged perspective view of parts of the device of FIG. 2 including the blunting member in portion A of FIG. 2;

FIG. 4 is a partial view on an enlarged scale of another embodiment of the invention in which an extension member is carried on the plunger head of the syringe;

FIG. 5 is a perspective view in cross section of a portion of another embodiment of the invention corresponding to portion A of FIG. 2;

FIG. 6 is a perspective view in cross section on an enlarged scale corresponding to portion A of FIG. 2, but of another embodiment of the invention; and FIG. 6A is a perspective view of a component of the embodiment of FIG. 6.

DETAILED DESCRIPTION OF THE INVENTION AND PREFERRED EMBODIMENTS

Figures 1D, 1E, 1F:
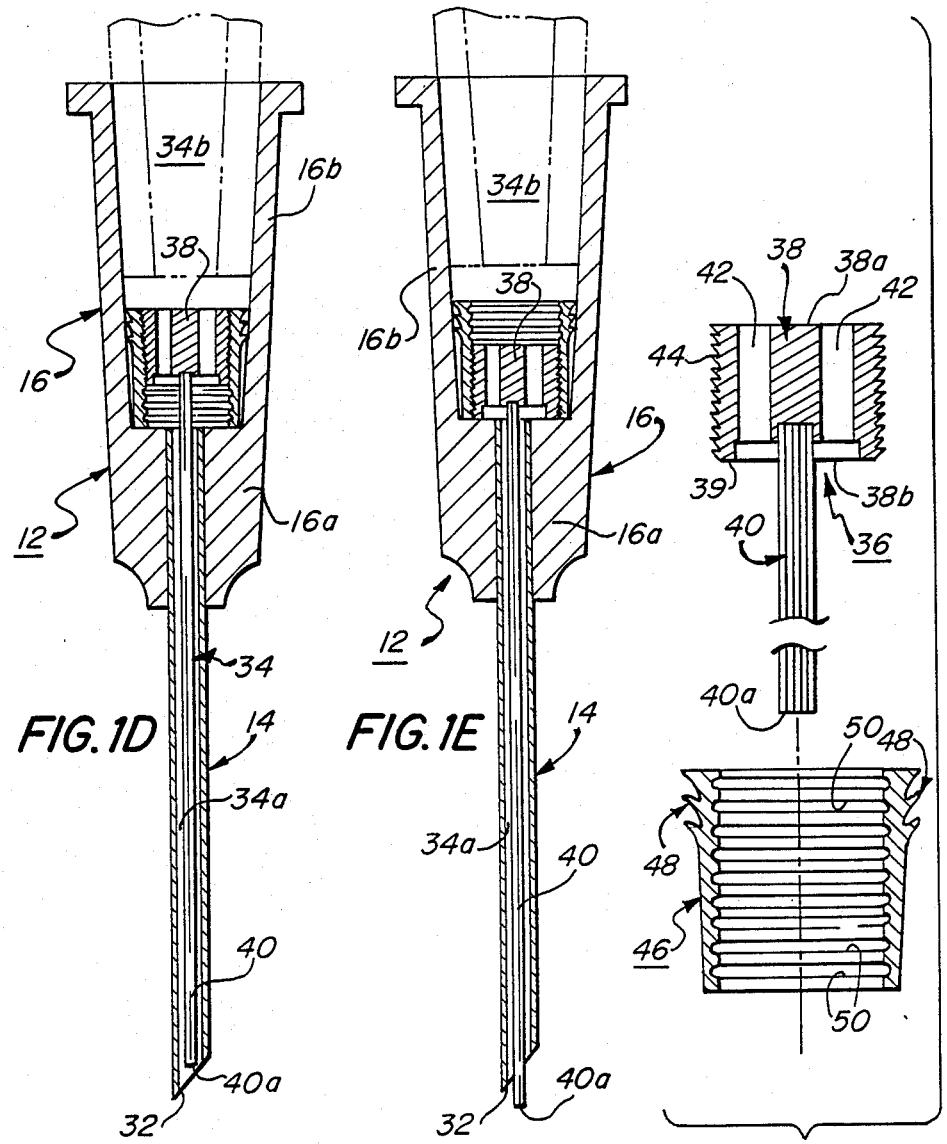
FIG. 1D shows on an enlarged scale the needle of FIG. 1 with the blunting member in its retracted position.
FIG. 1E is a view corresponding to FIG. 1D but showing the blunting member in its extended position to self-blunt the needle.
FIG. 1F is an exploded view, with a part broken away and on a further enlarged scale, of the blunting member and adapter of the needle member of FIG. 1.

Referring now to the drawings, FIG. 1 shows a hypodermic syringe generally indicated at 10 comprising a needle assembly generally indicated at 12 and attached to a plunger-type syringe 18. Needle assembly 12 includes a shank 14 attached at one end to a needle mouth 16 which is dimensioned and configured to be attached in fluid flow communication to the syringe 18.

Plunger-type syringe 18 comprises a barrel member 20 which is generally of hollow, cylindrical configuration and terminates in a barrel nozzle 22 of tapered configuration and of smaller diameter than the main bore 20a of barrel member 20. At the end of barrel member 20 opposite that which carries barrel nozzle 22, a finger rest 23 is provided in the form of a laterally extending rim or shoulder extending transversely of barrel member 20. A sealing plunger 24 is mounted for sliding, reciprocal movement within main bore 20a of barrel member 20 and is comprised of a plunger arm 26 having a thumb rest 28 at one end thereof and a plunger head 30 at the opposite end thereof. Plunger head 30 is made of rubber or soft plastic or other suitable material and is sized to provide a sliding seal within main bore 20a. Indicia I may be applied to barrel member 20 as illustrated in FIG. 1 to indicate the volume of liquid contained within main bore 20a. The structure and configuration of plunger-type syringe 18 is thus entirely conventional; plunger-type syringe 18 may be made from a suitable plastic (synthetic organic polymeric) material or it may be made of glass or metal or a combination of such materials.

Needle assembly 12, as best seen in the enlarged views of FIGS. 1D and 1E, is constructed with shank 14 having one end thereof embedded within a base portion 16a of needle mouth 16 by being fitted within a bore (unnumbered) extending through base portion 16a. A cup portion 16b of needle mouth 16 is sized to be mounted upon barrel nozzle 22 as illustrated in FIG. 1. Needle bore 34 extends through needle mouth 16 and shank 14 and has a shank portion 34a and a mouth portion 34b which is of larger diameter than the shank portion and defines the cup-like configuration of cup portion 16b. The end of shank 14 opposite that which is attached to needle mouth 16 terminates in a puncture tip 32 which, as is conventional, is formed at an angle to the longitudinal axis of shank 14 to provide a sharp puncture point in which the shank portion 34a of needle bore 34 (FIGS. 1A and 1C) terminates. Cup portion 16b has a floor or base 16c to which shank 14 and shank portion 34a of needle bore 34 extend, to place the shank portion 34a and mouth portion 34b of needle bore 34 into flow communication with each other. Needle mouth 16, like syringe 18, is thus of entirely conventional construction and may be made from any suitable material. It is one of the advantages of the present invention that conventional needles attachable to conventional syringes may readily be modified to be rendered self-blunting in accordance with the teaching of the present invention.

A blunting member 36 (FIGS. 1D, 1E and 1F) is mounted within needle mouth 16 and comprises a transfer means provided by a piston 38, and a probe 40 which terminates in a distal tip 40a. Piston 38 has a pressure side 38a, a probe side 38b from which probe 40 extends, and a plurality of flow passages 42 (best seen in FIGS. 1A, 1B and 1F) extending longitudinally therethrough. Probe side 38b, as best seen in FIGS. 1A and 1F, has a central recess formed therein to define a peripheral collar 39 (FIG. 1F) which protrudes axially of piston 38 so as to maintain flow passages 42 clear of floor 16c when piston 38 is seated thereon as illustrated in FIG. 1E. In this way, blockage or undue restriction of liquid flow through flow passages 42 is avoided. A plurality of detent means 44 (FIG. 1F) are formed about the periphery of piston 38. Detent means 44 may comprise a plurality of circular bands of shoulder-like protrusions which are wing- or wedge-shaped in cross-sectional profile, tapering from a thick cross section where they join the body of piston 38 to a thin, distal edge which faces in a direction away from probe 40, i.e., faces upwardly as viewed in FIGS. 1F and 1A.

An adapter thimble 46 (FIG. 1F) is of generally tubular construction and has formed about the exterior periphery thereof a plurality of mounting means 48 comprised of circular bands similar in construction to detent means 44. Mounting means 48 thus comprise resilient structures which are wing- or wedge-shaped in cross-sectional profile, tapering from a thick cross section where they join the body of thimble 46 to a thin distal edge, and which project outwardly from adapter thimble 46. Accordingly, when thimble 46 is wedged into place at the bottom (as viewed in FIGS. 1A, 1D and 1E) of cup portion 16b of needle mouth 16, the resilient tendency of mounting means 48 to extend outwardly of adapter thimble 46 is resisted by the interior wall of cup portion 16b, thereby firmly retaining adapter thimble 46 in place. In the case of needles which are manufactured specifically in accordance with the invention (as opposed to conventional needles which are adapted for use in the practice of the invention by insertion of a thimble 46 therein), the locking means may be made integral with needle mouth 16 or the base end of cup portion 16b may be made with detent members to firmly anchor thimble 46 in place. In any case, the interior of adapter thimble 46 has formed therein locking means 50 comprised of a series of circular indented peripheral bands. The bands of locking means 50 are sized and configured relative to the detent means 44 of piston 38 to readily permit piston 38 to travel within adapter thimble 46 in an outflow direction of needle mouth 16, i.e., in a direction moving from needle mouth 16 towards the puncture tip 32 of shank 14 but, because of the configuration and resiliency of detent means 44, will prevent the reverse direction of movement of piston 38, i.e., inflow movement in the direction from puncture tip 32 towards needle mouth 16.

Thus, a conventional needle mouth 16 of the type illustrated in FIGS. 1, 1D and 1E, may be adapted for purposes of the invention by inserting an adapter thimble 46 into cup portion 16b of needle mouth 16, forcing the adapter thimble 46 to the floor 16c of cup portion 16b, adjacent the mounted end of shank 14 as best seen in FIG. 1A. Blunting member 36 is then inserted into cup portion 16b of needle mouth 16 with probe 40 inserted into shank portion 34a of needle bore 34. Blunting member 36 may be positioned as illustrated in FIGS. 1A and 1D, with the top or pressure side of piston 38 (the side of piston 38 opposite that from which probe 40 extends) flush with the top of adapter thimble 46. Alternatively, blunting member 36 may be positioned with a portion of piston 38 protruding outwardly from the top of thimble adapter 46. Blunting member 36 will in any event be so positioned that the distal tip 40a (FIGS. 1D, 1E and 1F) of probe 40 will lie short of puncture tip 32 as illustrated in FIG. 1D.

With needle assembly 12 mounted on a plunger-type syringe 18 as illustrated in FIG. 1, the hypodermic syringe 10 is operated in the conventional manner. For example, puncture tip 32 may be injected through the seal of a bottle of liquid medication and plunger arm 26 retracted, i.e., moved in an upward direction as viewed in FIG. 1, to draw a required amount of medication into main bore 20a of barrel member 20. Blunting member 36 will remain stationary during this procedure because detent means 44 are engaged with locking means 50 and will retain blunting member 36 against movement by the inflowing liquid which passes through needle bore 34 through flow passages 42 in piston 38 thence into main bore 20a of barrel member 20. Typically, main bore 20a will be overfilled somewhat and a portion of the liquid expelled by moving plunger 24 downwardly to insure the expulsion of any air bubbles, the indicia on barrel member 20 being used as a guide to leave a premeasured quantity of liquid within main bore 20a. During this liquid expulsion step, blunting member 36 may move a small distance in an outflow direction. However, initial positioning of blunting member 36 is such as to allow for a limited amount of liquid outflow prior to distal tip 40a of probe 40 reaching the puncture tip 32.

Being thus prepared for use, hypodermic syringe 10 is then injected in the conventional manner into the patient and plunger 24 is pushed in the outflow direction (downwardly as viewed in FIG. 1) to expel the liquid from main bore 20a through needle bore 34 and flow passages 42 thence past puncture tip 32 and into the patient. In the embodiment illustrated, the diameter of probe 40, as best seen in FIG. 1C, is significantly less than the inside diameter of shank portion 34a of needle bore 34 so as to permit the flow of liquid through shank portion 34a in the annular space surrounding probe 40. Probe 40 is grooved in the illustrated embodiment, to provide additional annular flow space, and it alternatively may be of braided construction, for the same purpose. As liquid continues to move in the outflow direction, piston 38 is moved by the flowing liquid from the position shown in FIG. 1D to that shown in FIG. 1E, i.e., to the position in which piston 38 becomes seated at the base of cup portion 16b of needle mouth 16.

Figure 1G:
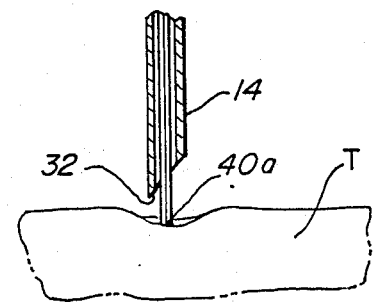
FIG. 1G is a partial view of the puncture tip end of the needle member in the self-blunted condition of FIG. 1E, pressed against tissue.

Detent means 44 are sufficiently flexible so that they can be deformed as piston 38 is moved in the outflow direction with a ratchet-like effect which permits piston 38 to move in the outflow direction under the force applied by the pressure drop of the expelled liquid flowing through flow passages 42, until the probe side of piston 38 is seated upon the floor 16c of cup portion 16b. At this point, as shown in FIG. 1E, distal tip 40a of probe 40 extends through shank 14 and outwardly of puncture tip 32. Distal tip 40a is of blunt configuration as best seen in FIG. 1F, and is locked in its extended position by the engagement of detent means 44 and locking means 50. Therefore, upon withdrawal of the needle from the patient puncture tip 32 is effectively blunted by the protruding distal tip 40a. As illustrated in FIG. 1G, the protruding distal tip 40a of probe 40 blunts the needle mouth 16, thereby preventing reentry of puncture tip 32 into tissue T in a needle-stick accident.

Referring now to FIGS. 2 and 2A, there is shown another embodiment of the invention wherein the transfer means is provided by an extension member which is mechanically actuated, rather than by a piston which is actuated by the liquid or fluid being transported through the device. Thus, a plunger-type syringe 18' is substantially identical to syringe 18 described with respect to the FIG. 1 embodiment and the corresponding parts thereof are identically numbered to those of FIG. 1 except for the addition of a prime indicator. Similarly, needle mouth 16' and shank 14' are constructed identically or similarly to the corresponding parts of the FIG. 1 embodiment.

Referring to FIG. 2A, an adapter thimble 46' is seated upon floor 16c' and mounted within cup portion 16b' a manner substantially identical to that explained in detail with respect to the embodiment of FIG. 1. However, in the embodiment of FIGS. 2 and 2A, blunting member 52 comprises a piston 54 having piston vent passages 55 extending therethrough and detent means (unnumbered, and best seen in FIG. 2A) formed about its periphery. The detent means of piston 54, which has a pressure side 54a and a probe side 54b connected by vent passage 55, correspond to detent means 44 of the FIG. 1 embodiment and are dimensioned and configured figured to engage locking means (unnumbered) corresponding to locking means 50 of FIG. 1A and formed on the interior of adapter thimble 46'.

A probe 56 extends from the probe side 54b of piston 54, terminates in a distal tip 56a thereof, and is received thin the shank portion 34a' of the needle bore. The needle bore is not separately numbered in FIGS. 2 and 2A (apart from shank portion 34a, thereof) but corresponds to needle bore 34 of FIG. 1D and of course extends entirely through the needle assembly 12'. Probe 56 is hollow and has a probe bore 58 extending therethrough. An extension member 60, which extends from the pressure side 54a of piston 54 and terminates in a distal tip 60a, is comprised of a segment of an integral member, the other side of which extends from probe side 54b as the probe 56. Obviously, the extension member 60 and the probe 56 could be comprised of two separate parts respectively joined to opposite sides of piston 54. Probe bore 58 extends through both probe 56 and extension member 60. Accordingly, in operation, as plunger 24' is moved downwardly, medication or other liquid contained within main bore 20a' is expelled through probe bore 58, passing through extension member 60 and then probe 56 for discharge from puncture tip 32'. When plunger head 30' engages the distal tip 60a of extension member 60, continued movement of plunger head 30' in the outflow direction forces extension member 60 and thus piston 54 downwardly until piston 54 is seated on floor 16c'; at this point, probe 56 is at its extended position, with its distal tip 56a protruding beyond puncture tip 32', in the manner illustrated in FIGS. 1E and 1G with respect to the FIG. 1 embodiment. Piston vent passages 55 allow liquid delivered to needle mouth 16' to displace air from chamber C formed between probe side 54b of piston 54 and floor 16c' of needle mouth 16'. During movement of blunting member 52 to its extended position, liquid in chamber C is expelled through piston vent passages 55 as chamber C is reduced in volume and then eliminated as piston 54 seats on floor 16c'. The detent means (unnumbered) associated with piston 54 and the locking means (unnumbered) associated with adapter thimble 46' permit movement in the outflow direction of piston 54, but prevent its return movement in the inflow direction so that probe 56 will be locked in its extended position, with piston 54 thereof in place in abutting contact with floor 16c'. In the illustrated embodiment, when plunger head 30' engages extension member 60 it will seal probe bore 58 against further liquid flow therethrough. In an alternative embodiment, the distal tip 60a of extension member 60 could be formed in a crenalated configuration, or holes could be provided in extension member 60 to provide flow passages to permit continued liquid expulsion therethrough after plunger head 30' engages extension member 60. In the embodiment illustrated in FIGS. 2 and 2A, liquid flow is through needle bore and probe bore 58. Alternatively, probe 56 could be made of a sufficiently small diameter to provide an annular liquid or fluid flow space between it and shank portion 34a of the needle bore. In such case, extension member 60 could be solid, the liquid flowing through piston flow passages 55.

Figure 3C:
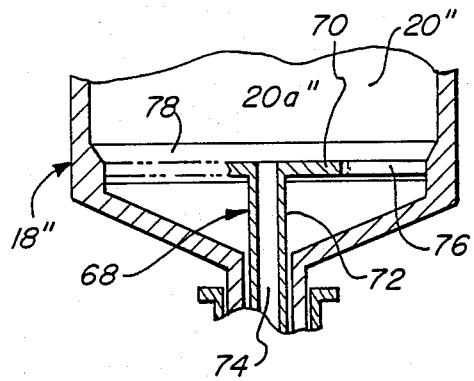
FIG. 3C is an enlarged view in cross section of portion C of FIG. 3.
Figure 3B:
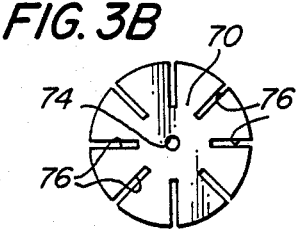
FIG. 3B is a plan view taken along line B—B of FIG. 3A.
Figure 3A:
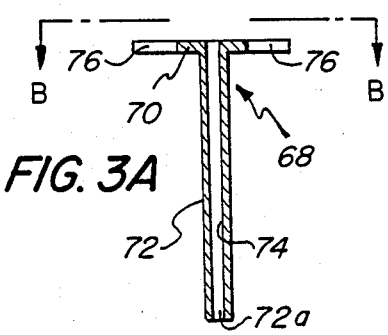
FIG. 3A is an elevation view in cross section of one component of the device of FIG. 3.
Figure 3D:
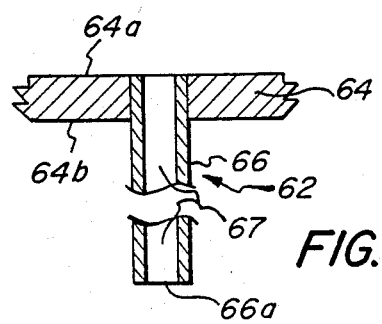
FIG. 3D is an enlarged view in elevation with parts broken away of another component of the device of FIG. 3.
Figure 3:
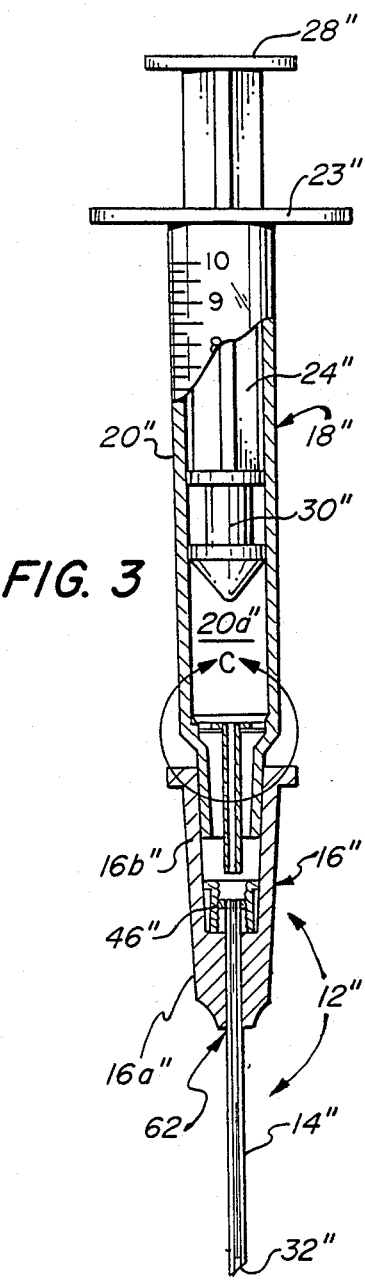
FIG. 3 is a view corresponding to FIG. 1 but showing yet another embodiment of the present invention.

Referring now to FIG. 3, there is shown yet another embodiment of the invention, including a plunger-type syringe 18" which is of substantially similar construction to syringes 18 and 18' of FIGS. 1 and 2 and a needle assembly 12" which is substantially similar in construction to needle assemblies 12 and 12' of FIGS. 1 and 2. Accordingly, corresponding parts are identically numbered to those of the FIGS. 1 and 2 embodiments, except for the indication of a double prime indicator. In this embodiment, blunting member 62 is similar in construction to blunting member 52 of the FIG. 2 embodiment, except that, as best seen in FIG. 3D, probe 66 terminates at the pressure side 64a of piston 64 and extends only from probe side 64b of piston 64. Probe 66 has a probe bore 67 extending therethrough and through piston 64 so that it extends through blunting member 62 to provide a liquid flow path therethrough, and terminates in distal tip 66a. As seen in FIG. 3, blunting member 62 is positioned initially flush with the top of adapter thimble 46", in the same relative position as illustrated in FIG. 1A with respect to blunting member 36. In this embodiment, a separate extension member 68 is provided and, as shown in FIGS. 3A, 3B and 3C, has a disc-shaped mounting head 70 at one end thereof and an extension arm 72 extending axially therefrom and through which an extension bore 74 extends. Extension bore 74 also extends through mounting head 70 and thus through the entire extension member 68. A plurality of radial slits 76 are formed in mounting head 70 and extend to the periphery thereof As best seen in FIG. 3C, extension member 68 is mounted within syringe 18" by mounting means provided by a circumferential mounting shoulder 78 protruding from the inside wall of barrel member 20" and having an inside diameter which is slightly smaller than the outside diameter of mounting head 70. Shoulder 78 is seen to have an upper (as viewed in FIG. 3C) inwardly tapering section and a lower constant diameter section. Extension member 68 may be made of plastic or a metal such as steel and mounting head 70, having the plurality of slits 76 formed therein, may readily be fitted in place by being force-fit against the inward tapering section of shoulder 78. Alternatively, a shallow groove may be formed within shoulder 78, generally conforming to the area indicated by dash lines in FIG. 3C, to snap-fit and hold extension member 68 in place until it is dislodged by plunger head 30" as described below.

In operation, as plunger 24" is pushed in the outflow direction, liquid contained within main bore 20a" is expressed through extension bore 74 (and slits 76) into needle mouth 16", thence through probe bore 67 of blunting member 62 for ejection past puncture tip 32". As plunger 24" approaches the end of its travel within barrel member 20", plunger head 30" engages mounting head 70 of extension member 68 and pushes it past shoulder 78, mounting head 70 and shoulder 78 being respectively dimensioned and configured to enable readily dislodging extension member 68 from shoulder 78. As extension member 68 is thus forced to move in the outflow direction, the distal end 72a of arm 72 thereof engages piston 64 of blunting member 62 and forces it in the outflow direction to move it and probe 66 from its retracted to its extended position, in which distal tip 66a of probe 66 protrudes past puncture tip 32" in a manner as illustrated in FIG. 1E with respect to the FIG. 1 embodiment. Thus, in the embodiment of FIG. 3, the extension member 68 is separate from the blunting member 62 but serves the same function as the integral extension member 60 of the FIG. 2 embodiment.

FIG. 4 shows yet another embodiment of the invention in which the extension member is separate from the blunting member but, in this embodiment, is mounted on and carried by the plunger head. Thus, a plunger 24''' comprises a plunger arm 26''' having a conventional mounting lug 84 on which a plunger head 82 is carried for sliding, sealing movement within a barrel member 20'''. Plunger head 82 is shown in cross section to reveal a conical-shaped head mounting recess 85 which serves to hold plunger head 82 in place on lug 84. Plunger head 82 also has a conical-shaped extension mounting recess 86 formed therein within which is mounted an extension member 88 which has a disc-shaped head 90 which is snap-fitted within recess 86. Plunger head 82 is made of a resilient, elastic material, such as rubber or a suitable soft plastic material, so that the respective openings (unnumbered) of recesses 85 and 86 may be deformed for insertion of, respectively, lug 84 and head 90 therein, and will then regain their original shapes to securely hold lug 84 and extension member 88 in place within plunger head 82. Extension member 88 has an elongate extension arm 92 extending therefrom; extension arm 92 terminates in a distal tip 92a and has a plurality of longitudinally extending grooves 94 formed therein. A needle assembly 12''' which, in the illustrated embodiment, is identical to needle assembly 12" of the FIG. 3 embodiment is mounted in fluid flow communication with barrel member 20'''. Needle assembly 12''' contains a blunting member 62" therein, which is substantially identical to the blunting member 62 of the FIG. 3 embodiment.

In operation, as plunger head 82 is advanced in the outflow direction forcing liquid contained within main bore 20a''' in the outflow direction through needle assembly 12''' for dispensing therefrom, downward movement is continued until the distal tip 92a of extension arm 92 engages the piston 64' of blunting member 62' and forces it in the outflow direction to move it from its retracted to its extended position as described above with respect to the FIG. 3 embodiment. As plunger 24''' approaches the end of its travel within barrel member 20''' and extension arm 92 enters a narrow barrel nozzle 22''', the grooves 94 enable the passage of liquid past extension arm 92 into and through needle assembly 12'''. In an alternative embodiment, barrel nozzle 22''' can be made of larger diameter as illustrated, for example, in the FIG. 3 embodiment, and a suitable guide means having flow passages formed therein could be positioned within barrel member 20''' adjacent barrel nozzle 22''' in order to receive and guide extension arm 92 into contact with piston 64' of blunting member 62'.

FIGS. 5 and 6 respectively show portions of two other embodiments of the invention; the portions shown generally correspond to portion A of FIGS. 1 and 2, i.e., the portion showing the piston of the blunting member received within an adapter thimble mounted in the needle mouth 16. Whereas the embodiments of FIGS. 1-4 illustrate devices in which the transfer means is dimensioned and configured to drive the blunting member from its retracted to its extended position by outflow movement of liquid along the flow path, e.g., when dispensing medication from the device into a patient or conduit, the embodiments of FIGS. 5 and 6 illustrate devices wherein the transfer means is dimensioned and configured to drive the blunting member from its retracted position to its extended position by inflow movement of liquid along the flow path. That is, the embodiments of FIGS. 5 and 6 will operate the blunting member when liquid is drawn into the device, such as when a blood sample is taken.

Referring now to FIG. 5, there is shown a section of the needle mouth 16, the base portion 16a of which contains the shank 14 of the needle assembly and cup portion 16b which defines the mouth portion 34b of the needle bore extending therethrough. In this embodiment, adapter thimble 96 is comprised of a cylindrical body portion 97 closed at one end by a disc-shaped end wall 98 having a flow passage 100 formed therein. Adapter thimble 96 is fitted within base portion 16a of needle mouth 16 by a rim portion 96a which is force-fitted within cup portion 16b of needle mouth 16. The open end of cylindrical body portion 97 opposite that closed by end wall 98 is seated upon floor 16c of needle mouth 16. Rim portion 96a may have resilient mounting means thereon, such as mounting means 48 of the embodiment illustrated in FIG. 1F. A blunting member 102 is comprised of a piston 104 and a probe 106 which is hollow to define a probe bore 108 which extends to and through piston 104. Piston 104 has a probe side 104b from which probe 106 extends and an opposite, pressure side 104a. Detent means 110 are formed about the periphery of piston 104 and are dimensioned and configured to engage locking means 112. Detent means 110 and locking means 112 are analogous to, and may be substantially identical to, detent means 44 and locking means 50, best seen in FIG. 1F. Piston 104 is positioned with pressure side 104a closely spaced from the inside surface of end wall 98 to form a pressure chamber P therebetween. At the end of body portion 97 adjacent to floor 16c, there is provided a plurality of first vent passages 114 which place the portion of adapter 96 which is enclosed beneath piston 104, into flow communication with an annular space 116 formed between the outer wall of adapter 96 and the inner wall of cup portion 16b. A plurality of second vent passages 118 are formed about the periphery of end wall 98 so as to place annular space 116 in flow communication with the mouth portion 34b of the needle bore.

The needle assembly of which needle mouth 16 forms a part is fitted onto any suitable barrel nozzle, such as barrel nozzle 22''' of the FIG. 4 embodiment.

In operation, the puncture tip (not shown) of the shank 14 is injected into a patient or other source of liquid so that the puncture tip enters, e.g., a vein, from which blood is to be drawn. The plunger of the barrel member (not shown) to which the needle assembly is attached is then moved in an inflow direction, i.e., in a direction away from needle mouth 16, thereby creating a partial vacuum or reduced pressure within the main bore of the barrel member and thus within mouth portion 34b of the needle bore. Blood, or other fluid being drawn, enters the shank 14 then passes through probe bore 108 into the pressure chamber P, between the pressure side 104a of piston 104 and the interior of end wall 98. The blood or other liquid being sampled will flow through the flow passage 100 through mouth portion 34b thence into the barrel member or other collector to which the needle assembly is attached. However, the rate of blood flow through flow passage 100 is attenuated because of the small flow diameter of passage 100, and the resultant pressure increase in the pressure chamber P will force piston 104 downwardly, thereby moving blunting member 102 and its associated probe 106 from its retracted position to its extended position to blunt the puncture tip as illustrated in FIG. 1G with respect to the FIG. 1 embodiment. As blood or other fluid is drawn through probe bore 108 into the chamber formed between piston 104 and end wall 98 and forces piston 104 downwardly, air trapped between piston 104 and floor 16c may escape through first vent passages 114 thence through annular space 116 and second vent passages 118. In the embodiment illustrated in FIG. 5, the interior walls of cup portion 16b, i.e., the walls defining mouth portion 34b of the needle bore, diverge outwardly in an inflow direction and the cylindrical body portion 97 of thimble adapter 96 may have a substantially constant, circular cross section. This configuration provides a tapering annular space 116. If cup portion 16b has a constant diameter mouth bore 34b, the cylindrical body portion 97 of adapter thimble 96 is made with a somewhat smaller diameter to provide the annular space 116. When piston 104 is driven downwardly to where it seats on floor 16c, the needle is blunted by the protrusion of the distal tip (not shown) of probe 106, but the device is capable of continuing to draw blood or the other sample being taken until the desired quantity of sample is received within any barrel member. At that point, the needle is withdrawn from the patient.

Referring now to FIGS. 6 and 6A, there is shown yet another embodiment of the present invention. In this embodiment, an adapter thimble 120 (FIG. 6A) comprises a cylindrical body portion 122 having a series of adapter flow passages 124 formed about the periphery of the base 126 thereof so that the base of body portion 122 has a crenalated appearance. An end wall 128 closes the end of cylindrical body portion 122 opposite the base 126 and is of larger diameter than the outside diameter of body 122 to provide a peripheral shoulder portion 128a having a circular shoulder sidewall 128b. A series of end wall apertures 130 are formed in end wall shoulder 128a and are equally angularly spaced about the periphery thereof. Adapter thimble 120 is force-fitted within a needle mouth 16 which, like needle mouth 16 of the FIG. 5 embodiment, includes a cup portion 16b and a base portion 16a having a floor or base 16c which is in communication with the bore of shank member 14. The force-fit within cup portion 16b is attained by engagement of shoulder sidewall 128b against the interior walls of cup portion 16b. As in all the other illustrated embodiments, cup portion 16b also serves to define mouth portion 34b of the needle bore. Locking means 132, similar to locking means 112 of the FIG. 5 embodiment, are formed on the interior wall of cylindrical body portion 122. Cylindrical body portion 122 is of smaller diameter than the inside diameter of mouth portion 34b within which it is positioned, to provide an annular space 125 between the inner wall of needle mouth 16 and the outer wall of cylindrical body portion 122.

A blunting member 134 comprises a piston 136 having a probe 138 extending radially therefrom, the peripheral sidewall of piston 136 having detent means 140 formed thereon. Detent means 140 and locking means 132 are respectively dimensioned and configured, and cooperate with each other in a manner described in detail with respect to the FIG. 1 embodiment, so that blunting member 134 can move in an outflow direction but is locked against retrograde movement in the inflow direction.

Probe 138 defines a probe bore 139 which extends therethrough from the distal tip (not shown) of probe 138 to and through piston 136. Piston 136 has a probe side 136b from which probe 138 extends into needle shank 14 in a manner similar to that shown and described in detail with respect to the embodiments of FIGS. 1, 2 and 3. Piston 136 has a pressure side 136a opposite probe side 136b, pressure side 136a and the interior of end wall 128 cooperating to define a pressure chamber P therebetween.

In operation, the needle assembly of which needle mouth 16 is a part is affixed to a suitable liquid transfer means such as a barrel member similar or identical to any one of the barrel members 20, 20', 20" or 20'". With the plunger of the barrel member in its fully extending outflow position, i.e., at the end of its range of travel towards the needle assembly, the shank 14 of the needle is injected into the patient or into a connector to withdraw a sample of body fluids, e.g., into a vein to draw a blood sample. The plunger is then raised, thus forming a partial vacuum or reduced pressure within the barrel member. Since end wall apertures 130 connect the annular space 125 with mouth portion 34b of the needle bore, a reduced pressure is effectuated within annular space 125 and this, in cooperation with the blood or other body fluid entering as shown by the unmarked arrows in FIG. 6, into the chamber P defined between piston 136 and end wall 128, forces blunting member 134 in an outflow direction, i.e., downwardly as viewed in FIG. 6. Liquid collects in the chamber between piston 136 and end wall 128 until outflow direction movement of piston 136 clears the adapter flow passages 124, thereby permitting the collected body fluids to flow through passages 124 thence through end wall apertures 130 into mouth portion 34b of the needle bore thence into the barrel member or other collecting device. At this point, blunting member 134 and its probe 138 will have advanced to and be locked in the extended position of probe 138, thereby self-blunting the puncture tip (not shown) of needle shank 14 in a manner as described and illustrated, for example, with respect to FIGS. 1E and 1G.

Tests with conventional hypodermic syringe needles have shown that even when utilizing a solid probe and flowing a liquid in the annular space between the solid probe and the inside walls of the shank portion of the needle bore, an adequate delivery rate of liquid may be attained. For example, stock hypodermic tubing (for the needle shank) made of T304/T316 stainless steel is commercially available in a wide range of gauges. An 18RW gauge steel hypodermic tubing has a nominal inside diameter of 0.033 inches. The manufacturer's specifications (All-Tube Division, a Microgroup Company, of Midway, Mass.) call for an inside diameter range of 0.0315 to 0.0345 inches. A solid probe as illustrated, for example, in FIG. 1A of the invention, preferably including the striations or flutings therein illustrated, and having a diameter of, e.g., about 0.020 to 0.028 inches will provide a satisfactory self-blunting probe. At a given pressure applied to the plunger of a syringe, a delivery rate of from about one-half to two-thirds of that which could be attained with an unencumbered needle bore is attained. A satisfactorily strong needle shank can also be made from 18XX gauge stainless steel stock hypodermic tubing which has a nominal inside diameter of 0.045 inches, the manufacturer's specifications calling for an inside diameter range of from 0.044 to 0.046 inches. Within this stock tubing a hollow probe made of 19XX gauge stock hypodermic tubing, which has a nominal outside diameter of 0.0425 inches, and a specification range of from 0.042 to 0.043 inches, may be utilized. The 19XX gauge stock tubing has a nominal inside diameter of 0.0375 inches, the specifications calling for an inside diameter range of from 0.0365 to 0.0385 inches. Thus, a hollow tube probe made of 19XX gauge stock hypodermic tubing will slidably fit within a needle shank made of 18XX gauge hypodermic tubing and provide a probe bore through which the liquid may be flowed, as illustrated in the embodiment of FIGS. 2 and 3, of from 0.0365 to 0.0385 inches. This is larger than the inside diameter of an unencumbered 18RW gauge needle. This arrangement thus provides a larger flow diameter through the probe bore than would be provided through a conventional needle made of 18RW gauge stock hypodermic tubing.

While various embodiments of the invention have been described with particular reference to hypodermic-type needles used primarily for injections directly into the body, those skilled in the art will appreciate that the invention is not so limited but, rather, is broadly applicable to provide self-blunting needles regardless of the use to which the needles are put. For example, it is common practice to connect a needle to a catheter or intravenous (IV) device by inserting the needle through a membrane seal of a catheter or IV-connecting device, which of course exposes the needle to the body fluids being transported through the catheter or IV-connecting device. Upon breaking the connection by removing the needle, an accidental needle stick wound can transmit infection from the needle, even though the needle was never directly injected into the patient's body because it nonetheless was contacted by the body fluids and/or medication for which it served as part of a conduit.

The invention is also broadly applicable to needles connected to liquid transfer devices other than syringes as illustrated in FIGS. 1, 2 and 3, for example, it is applicable to the needle assemblies designed to be injected directly into a patient and connected via a tube or other suitable connection to an IV bag or container, to a blood or other body fluid connector, or the like. Such needle assemblies may also be provided with a blunting device in accordance with the invention, which blunting device or at least the probe thereof may be moved from its retracted to its extended position either by liquid flow through the needle assembly or by mechanical manipulation. For example, an extension member may be fitted to an IV or blood bag needle and actuated just prior to removing the needle from the patient. Generally, the self-blunting action of the protruding probe has been found to be effective even when the probe protrudes a very small distance, as little as about fifty one-thousandths (0.050) of an inch, beyond the most distal portion of the puncture tip. Accordingly, in most, if not all, cases no patient discomfort or harm will be sustained by having the probe in its extended, self-blunting position while the needle is still within the patient's body. Nonetheless, at least the mechanical-actuating aspects of the invention permit deferring movement of the probe to its extended position until immediately prior to removing the needle from the patient. Alternatively, when equipped with a mechanical actuating device of the type illustrated in FIGS. 2 and 3, the blunting member may be moved to its extended, self-blunting position simultaneously with or immediately after removal from the patient. However, this technique involves the risk, albeit a minimal one, of an accidental needle-stick wound sustained in the act of removing the needle just prior to actuating the self-blunting device. Normally, it is preferable and causes no discomfort or harm to the patient to have the blunting device moved to its extended position prior to removal of the needle from the patient, at any time from immediately after injection of the needle into the patient to immediately prior to withdrawing it.

Generally, suitable configurations of the invention may be utilized with any liquid transfer means. For example, vacuum tubes are known for utilization in the taking of body fluid samples, such as blood samples. In such devices, a needle is injected into a patient's vein and a sealed tube from which air has been evacuated is mounted on a connector which penetrates a vacuum seal member, such as a membrane, on an open end of the tube. This exposes the needle to the vacuum or reduced pressure within the tube which acts in concert with the patient's blood pressure to fill the tube with a blood sample. The needles of the invention are of course adaptable for use with such vacuum tube sampling devices as well as with any liquid transfer means including conventional plunger-type syringes, squeeze bulb syringes, vacuum sampling devices or pressurized fluid-dispensing devices.

Needles of the invention have broad utility for medical, veterinary and other uses, such as autopsies and preparation of bodies for interment, generally whenever and wherever a needle must be injected into tissue or into a connector or other device in which the needle and/or its tip is exposed to contamination, and it is desired to blunt the needle to prevent reinjection of it. The prevention of reinjection prevents both deliberate reuse and accidental needle stick-wounds with a potentially contaminated needle.

Although the above-described embodiments use a mechanical or fluid force imposed axially on the blunting member to advance it to its extended position, a rotational action may also be utilized to axially advance the blunting member. Thus, the blunting member may carry turbine-like blades as part of the transfer means and be mounted in a screw-threaded bore so that the blades are rotated by liquid passing thereover to rotate the blunting member. Rotation of the blunting member within the screw-threaded bore axially advances the probe to its extended position.

For example, a screw-thread may be carried on the piston of the blunting member and be received in a threaded bore so that movement of liquid past the blades of the transfer means rotates the screwthread to drive the blunting member probe from its retracted to its extended position.

While the invention has been described in detail with reference to specific preferred embodiments thereof, it will be appreciated that such specific embodiments are illustrative only and the scope of the invention is more fully described in the appended claims

What is claimed:

1. A self-blunting needle assembly device suitable for attachment to a fluid flow means comprises:
   (a) a needle member terminating in a puncture tip and having a needle bore extending therethrough and defining a fluid flow path extending through the needle to the puncture tip;
   (b) a blunting member comprising an elongate probe having transfer means associated therewith, the blunting member being mounted within the needle member for movement of the probe by the transfer means axially along the needle bore from a retracted position in which the probe is short of the puncture tip to an extended position in which the probe protrudes outwardly of, and thereby blunts, the puncture tip, the probe being dimensioned and configured to be accommodated within the needle bore while leaving the bore open to fluid flow therethrough; and
   (c) locking means dimensioned and configured to engage the blunting member so as to permit its movement in an outflow direction but prevent its return movement in an inflow direction, whereby to retain it in its extended position.

2. The device of claim 1 wherein the transfer means comprises an extension member mounted within the needle member to transfer mechanical force applied to the extension member to the blunting member for movement thereof to its extended position.

3. A self-blunting needle assembly device suitable for attachment to a fluid flow means comprises:
   (a) a needle member terminating in a puncture tip and having a needle bore extending therethrough and defining a fluid flow path extending through the needle to the puncture tip;
   (b) a blunting member comprising an elongate probe having associated therewith transfer means comprising a piston form which the probe axially extends, the blunting member being mounted with its piston disposed in the fluid flow path, whereby liquid flowing through the flow path acts on the piston to move the blunting member axially along the needle bore from a retracted position in which the probe is short of the puncture tip to an extended position in which the probe protrudes outwardly of, and thereby blunts, the puncture tip, the probe being dimensioned and configured to be accommodated within the needle bore while leaving the bore open to fluid flow therethrough; and
   (c) locking means dimensioned and configured to engage the blunting member and retain it in its extended position.

4. In a hypodermic syringe device comprising (i) a hollow needle member having a shank which terminates in a puncture tip and through which a needle bore extends, (ii) a barrel member providing a liquid reservoir and connected in fluid flow communication with the needle member, and (iii) pressurizing means to impel fluid comprising a liquid along a fluid flow path including the barrel member and the needle bore, the improvement comprising:
   (a) a blunting member comprised of an elongate probe having a transfer means associated therewith, the probe being dimensioned and configured to be accommodated within the needle bore while leaving the bore open to liquid flow therethrough, the blunting member being mounted in the device for movement of the probe by the transfer means axially along the needle bore from a retracted position in which the probe is short of the puncture tip to an extended position in which the probe protrudes outwardly of, and thereby blunts, the puncture tip, and
   (b) locking means carried within the hypodermic syringe device and dimensioned and configured to engage the blunting member and retain it in its extended position.

5. The device of claim 4 wherein the transfer means comprises a piston from which the probe axially extends, the blunting member being mounted with its piston disposed in the fluid flow path whereby liquid flowing through the flow path acts on the piston to move the blunting member to its extended position.

6. The device of claim 2 or claim 5 wherein the piston has one or more flow passages extending therethrough to permit the passage of fluid along the flow path past the piston.

7. The device of claim 3 or claim 5 wherein the piston has a probe side from which the probe extends and an opposite pressure side, and further has one or more piston flow passages formed therein to admit fluid therethrough between the pressure side and the probe side.

8. The device of claim 1, claim 3, claim 4 or claim 5 wherein the transfer means is dimensioned and configured to drive the blunting member from its retracted position to its extended position by outflow of fluid along the flow path.

9. The device of claim 1, claim 3, claim 4 or claim 5 wherein the transfer means is dimensioned and configured to drive the blunting member from its retracted position to its extended position by inflow of fluid along the flow path.

10. The device of claim 4 wherein the transfer means comprises an extension member mounted within the needle member to transfer mechanical force applied to the extension member to the blunting member for movement thereof to its extended position.

11. The device of any one of claims 1 through 10 wherein the probe and the needle bore are each dimensioned and configured to provide therebetween an annular clearance for passage of fluid around the probe and through the needle bore.

12. The device of any one of claims 1 through 10 wherein the blunting member has a probe bore extending therethrough to define at least a segment of the fluid flow path through the needle member.

13. The device of any one of claims 1 through 10 wherein the locking means comprises a detent member and a detent recess, one of which is carried on the blunting member and the other of which is disposed within the needle member, the detent member and detent recess being dimensioned and configured to engage each other so as to prevent movement of the blunting member in the direction from its extended position towards its retracted position.

14. The device of claim 13 wherein the transfer means comprises a piston from which the probe axially extends and one of the detent member and detent recess is carried on the piston and the other is carried on a cylindrical thimble within which the piston is mounted for axial movement.

15. The device of any one of claims 1 through 10 wherein the needle member has a mouth dimensioned and configured to attach the needle assembly in fluid flow communication to a fluid transfer means, and the locking means is disposed within the needle mouth.

16. The device of claim 4, claim 5 or claim 10 wherein the pressurizing means comprises a sealing plunger mounted for sliding movement within the barrel member 17. The device of claim 10 wherein the piston has a probe side from which the probe extends and an opposite, pressure side, and the extension member is mounted on the piston and extends from the pressure side thereof.

18. A self-blunting needle assembly device suitable for attachment to a fluid flow means comprises:
(a) a needle member terminating in a puncture tip and having a needle bore extending therethrough and defining a fluid flow path extending through the needle to the puncture tip, the needle member having a mouth dimensioned and configured to attach the needle assembly in fluid flow communication to a fluid transfer means;
(b) a blunting member comprising an elongate probe having associated therewith transfer means comprising a position from which the probe axially extends, the blunting member being mounted with its piston disposed in the fluid flow path, whereby liquid flowing through the flow path acts on the piston to move the blunting member axially along the needle bore form a retracted position in which the probe is short of the puncture tip to an extended position in which the probe protrudes outwardly of, and thereby blunts, the puncture tip, the probe being dimensioned and configured to be accommodated within the needle bore while leaving the bore open to fluid flow therethrough; and
(c) locking means comprising a cylindrical thimble within which the piston is mounted for axial movement, said locking means being disposed within the needle mouth and being dimensioned and configured to engage the blunting member and retain it in its extended position.

19. A self-blunting needle assembly device suitable for attachment to a fluid flow means comprises:
(a) a needle member terminating in a puncture tip and having a needle bore extending therethrough and defining a fluid flow path extending through the needle to the puncture tip;
(b) a blunting member comprising an elongate probe having associated therewith transfer means comprising a piston from which the probe axially extends, the blunting member being mounted with its piston disposed in the fluid flow path, whereby liquid flowing through the flow path acts on the piston to move the blunting member axially along the needle bore from a retracted position in which the probe is short of the puncture tip to an extended position in which the probe protrudes outwardly of, and thereby blunts, the puncture tip, the probe being dimensioned and configured to be accommodated within the needle bore while leaving the bore open to fluid flow therethrough;
(c) locking means dimensioned and configured to engage the blunting member and retain it in its extended position; and
(d) a pressure chamber within which the piston is mounted, the pressure chamber being in flow communication with (i) at least one chamber inlet passage to admit fluid from the needle member into the pressure chamber and (ii) with at least open chamber outlet passage to permit fluid to escape from the pressure chamber, the inlet and outlet passages having respective flow diameters dimensioned and configured to increase fluid pressure within the pressure chamber so as to drive the blunting member from its retracted position to its extended position.

20. The device of claim 19 wherein the chamber outlet passage has a smaller total cross-sectional flow area than the total cross-sectional flow area of the chamber inlet passage.

21. The device of claim 19 wherein the pressure chamber is dimensioned and configured to drive the blunting member from its retracted position to its extended position by outflow of fluid along the flow path.

22. The device of claim 19 wherein the pressure chamber is dimensioned and configured to drive the blunting member from its retracted position to its extended position by inflow of fluid along the flow path.

23. The device of claim 19 wherein the piston has a probe side from which the probe extends, the needle has a needle mouth within which an adapter is mounted, and the adapter is dimensioned and configured (a) to cooperate with the piston to define the pressure chamber between the adapter and the piston and (b) to expose the probe side of the piston to suction imposed on the needle mouth whereby the suction cooperates with pressure generated within the pressure chamber to impact a net force acting on the piston to urge it towards its extended position.

24. The device of claim 19 wherein the piston has a probe side from which the probe extends and an opposite pressure side, the piston is mounted within an adapter which cooperates with the piston to define the pressure chamber between the adapter and the pressure side of the piston, and the adapter has vent passages formed therein to vent the space formed between the adapter and the probe side of the piston.

25. A self-blunting needle assembly device suitable for attachment to a fluid flow means comprises:
(a) a needle member terminating in a puncture tip and having a needle bore extending therethrough and defining a fluid flow path extending through the needle to the puncture tip;
(b) a blunting member comprising an elongate probe having associated therewith transfer means comprising a piston having piston flow passages extending therethrough, the blunting member including a probe bore extending therethrough to define at least a segment of the fluid flow path through the needle member, the blunting member being mounted within the needle member for movement of the probe by the piston axially along the needle bore from a retracted position in which the probe is short of the puncture tip to an extended position in which the probe protrudes outwardly of, and thereby blunts, the puncture tip, the probe being dimensioned and configured to be accommodated within the needle bore while leaving the bore open to fluid flow therethorugh;
(c) locking means dimensioned and configured to engage the blunting member and retain it in its extended position; and
said needle having a needle mouth having a floor, the piston being mounted within the needle mouth for seating on the floor thereof when the blunting member is in its extended position, and the piston having a stop member projecting axially from the probe side thereof to space the piston flow passages from the floor when the blunting member is in its extended position.

26. In a hypodermic syringe device comprising (i) a hollow needle member having a shank which terminates in a puncture tip and through which a needle bore extends, (ii) a barrel member providing a liquid reservoir and connected in fluid flow communication with the needle member, and (iii) pressurizing means to impel fluid comprising a liquid along a fluid flow path including the barrel member and the needle bore, the improvement comprising:
(a) a blunting member comprised of an elongate probe having a transfer means associated therewith, the probe being dimensioned and configured to be accommodated within the needle bore while leaving the bore open to liquid flow therethrough, the blunting member being mounted in the device for movement of the probe by the transfer means axially along the needle bore from a retracted position in which the probe is short of the puncture tip to an extended position in which the probe protrudes outwardly of, and thereby blunts, the puncture tip; and
(b) locking means dimensioned and configured to engage the blunting member and retain it in its extended position;
the transfer means comprising an extension member mounted within the needle member to transfer mechanical force applied to the extension member to the blunting member for movement thereof to its extended position, the extension member being separate from and independent of the blunting member and slidably mounted in alignment with the blunting member for movement into engagement therewith to move the blunting member from its retracted to its extended position.

27. The device of claim 26 including a plunger dimensioned and configured to mechanically force fluid through the needle member, and the extension member is mounted on the plunger.

28. A self-blunting needle assembly device comprises:
(a) a needle member terminating in a puncture tip and having a needle bore extending therethorugh and defining a fluid flow path extending through the needle to the puncture tip;
(b) a blunting member comprising an elongate probe having transfer means associated therewith, the blunting member being mounted within the needle member for movement of the probe by the transfer means axially along the needle bore from a retracted position in which the probe is short of the puncture tip to an extended position in which the probe protrudes tip to an extended position in which the probe protrudes outwardly of, and thereby blunts, the puncture tip, the probe being dimensioned and configured to be accommodated within the needle bore while leaving the bore open to fluid flow therethrough; and
(c) locking means carried within the needle member and dimensioned and configured to engage the blunting member and retain it in its extended position.

29. The device of claim 28 wherein the transfer means comprises a piston form which the probe extends, the device includes a needle mouth suitable for attachment to a fluid flow means, and the locking means is disposed within the needle mouth and is dimensioned and configured to therein engage and retain the piston.

* * * * *